United States Patent [19]

Watson et al.

[11] Patent Number: 5,221,314

[45] Date of Patent: Jun. 22, 1993

[54] **SYNERGISTIC HERBICIDAL COMPOSITIONS COMPRISING *COLLETOTRICHUM COCCODES* AND CHEMICAL HERBICIDES**

[75] Inventors: Alan K. Watson, Pincourt, Canada; Alan R. Gotlieb, Essex Junction, Vt.

[73] Assignee: The Royal Institution for the Advancement of Learning (McGill University), Quebec, Canada

[21] Appl. No.: 304,146

[22] Filed: Jan. 31, 1989

Related U.S. Application Data

[60] Continuation-in-part of Ser. No. 113,703, Oct. 28, 1987, Pat. No. 4,808,207, which is a division of Ser. No. 9,001, Jan. 27, 1987, Pat. No. 4,776,873, which is a continuation of Ser. No. 747,511, Jun. 21, 1985, abandoned.

[51] Int. Cl.⁵ ............................................. A01N 63/00
[52] U.S. Cl. ..................................................... 504/117
[58] Field of Search ................. 71/79, 92, 90, 115, 71/117, 114, 118, 93, 111, 86

[56] References Cited

U.S. PATENT DOCUMENTS

| | | | |
|---|---|---|---|
| 3,849,104 | 11/1974 | Daniel et al. | 71/79 |
| 3,999,973 | 12/1976 | Templeton | 71/79 |
| 4,162,912 | 7/1979 | Charudattan | 71/79 |
| 4,263,036 | 4/1981 | Charudattan | 71/79 |
| 4,390,360 | 6/1983 | Walker | 71/79 |
| 4,419,120 | 12/1983 | Walker | 71/79 |
| 4,715,881 | 12/1987 | Anderson et al. | 71/79 |
| 4,775,405 | 10/1988 | Caulder et al. | 71/79 |
| 4,776,873 | 10/1988 | Caulder et al. | 71/79 |

OTHER PUBLICATIONS

Scheepens et al., "Microbial Herbicides," *Microbial and Viral Pesticides* (Mercel Dekker, Inc., New York), 1982, pp. 623–629.
Wade, U.S. patent application Ser. No. 06/392,364 (published in *Chem. Abstracts*, vol. 101, 1984, Feb. 7).
Klerk et al., "Interaction of Pesticides with Mycoherbicide . . . ", *Proc. S.W. Weed Sci. Soc.* (35:68, 1982).
Dale, U.S. patent application Ser. No. 06/555,749 (published in *Chem. Abstracts* vol. 101, 1984, Mar. 16).
Altman, J. et al., "Effect of Herbicides on Plant Diseases", Annual Review of Phytopathology, vol. 15, 1977, pp. 361–385.

*Primary Examiner*—Allen J. Robinson
*Assistant Examiner*—Brian M. Burn
*Attorney, Agent, or Firm*—Cushman, Darby & Cushman

[57] ABSTRACT

Disclosed are compositions and processes for controlling velvetleaf. These compositions comprise synergistic compositions of a *Colletotrichum coccodes* and chemical herbicides. Use of the synergistic compositions of the subject invention enhances the value of the *Colletotrichum coccodes* by reducing the amount of herbicide needed and by extending the range of environmental conditions in which the *Colletotrichum coccodes* will function.

4 Claims, No Drawings

SYNERGISTIC HERBICIDAL COMPOSITIONS COMPRISING *COLLETOTRICHUM COCCODES* AND CHEMICAL HERBICIDES

CROSS REFERENCE TO RELATED APPLICATIONS

This application is a continuation-in-part of copending application Ser. No. 113,703, filed Oct. 28, 1987, now U.S. Pat. No. 4,808,207, issued Feb. 28, 1989, which is a divisional of application Ser. No. 009,001, filed Jan. 27, 1987, now U.S. Pat. No. 4,776,873, issued Oct. 11, 1988; which is a continuation of application Ser. No. 747,511, filed Jun. 21, 1985, now abandoned.

BACKGROUND OF THE INVENTION

Weeds cost farmers billions of dollars annually in crop losses and in the expense of keeping the weeds under control. The losses caused by weeds in agricultural production environments include decrease in crop yield, reduced crop quality, increased irrigation costs, increased harvesting costs, decreased land value, injury to livestock, and crop damage from insects and diseases harbored by these weeds.

Chemical herbicides have provided an effective method of weed control in the past. However, the public has become concerned about the amount of chemicals applied to the food that they consume, to the land on which they live, and to the ground water which they use. Stringent restrictions on the use and development of new herbicides and the elimination of some effective herbicides from the market place have limited economical and effective means for controlling costly weed problems.

A problem has been identified after years of use of chemical herbicides on commercial agricultural land, i.e., the lack of control of certain weeds has allowed these weeds to take over the areas where, without the use of chemical herbicides, they were excluded by more hardy weeds. Removal of the more competitive weeds with chemical herbicides has left an ecological void that has been filled by the less competitive weeds that are resistant to the herbicides. Weeds that were of minor importance at one time have spread rapidly throughout the areas where they are found and are now considered major weed problems. In addition to the inadequacy of control of all weeds, chemicals also can damage the crop plants, sometimes injure nontarget organisms in the environment, and can leave undesirable residues in water and harvested products and carry-over in subsequent crops.

Microbial herbicides are plant pathogens which are effective, when used according to the process disclosed herein, in controlling weeds or other undesirable vegetation without adversely affecting the growth and yield of the desired field crop. The composition of a microbial herbicide includes spores or cells of the plant pathogen or any portion of the organism that is capable of infecting the weed. The use of microbial herbicides is becoming an increasingly important alternative to chemical herbicides. This importance is accompanied by the issuance of several patents for microbial herbicides and their use. Some of these patents, by way of illustration, are as follows: U.S. Pat. No. 3,849,104 (control of northern jointvetch with *Colletotrichum gloeosporioides* Penz. aeschynomene); U.S. Pat. No. 3,999,973 (control of prickly sida [teaweed] and other weeds with *Colletotrichum malvarum*); U.S. Pat. No. 4,162,912 (control of milkweed vine with *Araujia mosaic* virus); U.S. Pat. No. 4,263,036 (control of *Hydrilla verticillata* with *Fusarium roseum* Culmorum); U.S. Pat. No. 4,390,360 (control of sicklepod, showy crotalaria, and coffee senna with *Alternaria cassiae*); and U.S. Pat. No. 4,419,120 (control of prickly sida, velvetleaf, and spurred anoda with fungal pathogens); U.S. Pat. No. 4,775,405 (control of Florida beggarweed with a mixture of *Colletotrichum truncatum* and chemical herbicides); and U.S. Pat. No. 4,776,873 (control of sicklepod with a mixture of *Alternaria cassiae* and a chemical herbicide).

We have discovered that mixtures of *Colletotrichum coccodes* and certain chemical herbicides, are synergistic in their activity when applied to the foliage of the host weed of *C. coccodes*. This synergy will greatly increase the value of *C. coccodes* by reducing the amount of *C. coccodes* applied, and reducing the environmental limitations of *C. coccodes*. At the Weed Science Society of America meeting in Feb. 2–4, 1988, we disclosed the synergy between *C. coccodes* and the chemical herbicides fomesafen, dicamba, 2,4-D, and AC 263,499.

BRIEF SUMMARY OF THE INVENTION

The subject invention concerns the unexpected discovery that mixtures of *Colletotrichum coccodes* and certain chemical herbicides produce a synergistic effect against velvetleaf. There is no known way to predict which chemical herbicides would be synergistic in mixture with *C. coccodes*. This synergistic effect significantly enhances the value of *C. coccodes* by reducing the amount of *C. coccodes* needed and by extending the range of environmental conditions in which *C. coccodes* will function.

The activity of a microbial herbicide is sensitive to fluctuations in the environment. The majority of the examples which support our discoveries were carried out under greenhouse conditions. The environmental conditions within the greenhouse are more constant than the ambient environment outside the greenhouse. However, the environment within the greenhouse fluctuates daily and the interaction between a microbial herbicide and its host also varies with these changes in environment. The sensitivity of microbial herbicides to environmental fluctuations is one of the major constraints in commercializing a microbial herbicide. This sensitivity to environment explains the lack of consistent control when the same rate of microbial herbicide was applied to weeds on different days. This sensitivity to environment is reduced when the microbial herbicide is combined with a chemical herbicide. The result is effective weed control under a wide range of environmental conditions.

Generally, in the practice of the subject invention, *C. coccodes* can be applied at rates between 10E7 to 10E12 propagules per acre, and the chemical herbicide can be applied at rates of ½ to 1/32 the rate recommended for weed control on the label of the compound in accordance with EPA regulations, against the target weed. If desired, the chemical herbicides can be used at recommended full rates to achieve a broader spectrum of weed control.

DETAILED DESCRIPTION OF THE INVENTION

The synergistic mixtures of *Colletotrichum coccodes* and chemical herbicides of the subject invention make possible the control of weeds which cannot be effectively controlled by either the microbial herbicide or the chemical herbicide alone. *Colletotrichum coccodes* of the subject invention includes *Colletotrichum coccodes* Wallr. (DAOM 183088) against the weed *Abutilon theophrasti* Medic. (velvetleaf).

The *C. coccodes* of the subject invention are known fungi, as disclosed above. These fungi can be grown and formulated for use as microbial herbicides by procedures well known in the art.

Listed in Table A are chemical herbicides.

TABLE A

| Trade Name | Chemical Name | Common Name |
| --- | --- | --- |
| AATREX | 6-chloro-N-ethyl-N'-(1-methylethyl)-1,3,5-triazine-2,4-diamine; 2-chloro-4-ethylamino-6-isopropylamine-s-triazine | atrazine |
| BASAGRAN | Sodium salt of (3-isopropyl-1 H-2,1,3-bentzothiadiazin-4 (3H)-one 2,2-dioxide) | bentazon sodium salt |
| BLAZER | Sodium s-(2-chloro-4 trifluoromethyl)-phenoxyl-2-nitrobenzoate | acifluorfen sodium salt |
| CLASSIC | 2-(([(4-chloro-6-methoxpyrimidine-2-yl)amino carbonyl] amino sulfonyl))benzoic acid ethyl ester | chlorimuron (DPX-F6025) |
| BANVEL | 3,6-dichloro-anisic acid | dicamba |
| Several | (2,4-diclorophenoxy) acetic acid | 2,4-D |
| PURSUIT | 5-ethyl-2-(4-isopropyl-4-methyl-5-oxo-imidazolin-2-yl) nicotinic acid | AC 263,499 (imazethapyr) |
| HARMONY | (3-[[[(4-methoxy-6-methyl-1, 3,5-triazin-2-yl) amino carbonyl] amino] sulfonyl]-2-thiophencarboxylic acid) | DPX M6316 (thiameturon) |
| REFLEX | 5-[2-dichloro-4-(trifluoromethyl) phenoxy]-N-(methyl-sulfonyl)-2-nitrobenzamide | fomesafen |
| AMBER | 2-(2-chloroethoxy)-N-[L(4-methoxy-6-methyl-1,3,5-triazin-2-yl] amino carbonyl benzenesulfonamide | triasulfuron |
| BUTYRAC | 4-(2,4-dichlorophenoxy) butanoic acid | 2,4-DB |
| COBRA | 1'-(carboethoxy) ethyl 5-[2-chloro-4-(trifluoromethyl) phenoxy]-2-nitrobenzoate | lactofen |
| ROUNDUP | N-(phosphonomethyl) glycine | glyphosate |

The three major steps in plant pathogenesis are germination, penetration, and establishment of the pathogen within the host. Germination and penetration are the most environmentally sensitive stages. Colletotrichum spp. penetrate in the plant surface; Colletotrichum spp. penetrate actively after formation of appressoria (specialized structures which attach to the host surface and release enzymes which dissolve the cuticle and wall materials, allowing penetration of the infective hyphae) and through wounds in the plant surface.

The results of synergy experiments are summarized in Table B. Plus notation (+) in Table B indicates chemical herbicide synergism with *Colletotrichum coccodes*. A detailed explanation of each experiment is disclosed in the Examples which follow.

TABLE B

| | Synergy with | | | |
|---|---|---|---|---|
| Chemical | AC | CC | CT | FL |
| Basagran | + | + | + | + |
| Blazer | + | + | + | + |
| Classic | − | + | − | |
| Dicamba | | + | | |
| AC 263,499 | | + | | |
| DPX M6316 | | + | | |
| 2,4-D | | + | | |
| Atrazine | | + | | |
| Fomesafen | | + | | |
| Triasulfuron | | + | | |

The suppliers for the above chemical herbicides are as follows:

TABLE C

| Trade Name | Supplier |
|---|---|
| Basagran | BASF Wyandotte Corp. |
| Blazer | Rohm and Haas |
| Classic | Dupont |
| Dicamba | Sandoz (Velsicol) |
| AC 263,499 | American Cyanamid |
| DPX M6316 (HARMONY) | DuPont |
| 2,4-D | Several suppliers |
| Atrazine | Ciba Geigy |
| Fomesafen | ICI American |
| Triasulfuron | Ciba Geigy |

The objective of formulating herbicides is to provide the correct combination of ingredients so that the active component is suitable for application and optimum activity. Microbial herbicides have been formulated as dusts, wettable powders, granules, and suspensions.

Wettable powder formulas of Colletotrichum are composed of a diluent, wetting agent, and dispersant. Wetting agents and dispersants are surface active agents (surfactants) which reduce surface tension and promote homogenous distribution during application. A comprehensive list of surfactants is found in McCutcheon's Emulsifiers & Detergents 1985. Three to five percent of each is needed in the formula to ensure performance of the microbial herbicide. The diluents modify the formula to improve handling, storage, and application. Diluents that have been mixed with microbial herbicides are clays (attapulgite, montmorillonite, kaolinite), non-phyllosilites (talc, diatomaceous earth, vermiculite, synthetic bulking agents) and botanicals (grain flours, ground plant parts).

The formulation and application of the chemical herbicides, disclosed herein, are well known to those skilled in the art. See Herbicide Handbook of the Weed Science Society of America, Fifth Edition, 1983. This handbook is published by Weed Science Society of America, 309 West Clark Street, Champaign, Ill. 61820. Also, instructions for the formulation and use of individual chemical herbicides are disclosed on the product labels for the herbicides.

Several conventions are used in the following Examples to simplify the data tables and discussions. Abbreviations are utilized to designate the location and type of trial (Loc-Type), the name of the microbial herbicides, and the names of the weeds. These abbreviations will be described below.

Experiments are separated by location and type of trial. The location abbreviations and corresponding description are: CA—California, FL—Florida, IL—Illinois, ML—Montreal, VT—Vermont. The control of environment is indicated by the type of trial: C—controlled environment growth chamber (highly controlled environment, temperature, and light); G— greenhouse conditions (moderate control of temperature, little control of light); F—field conditions (no control of temperature, light, or relative humidity).

California: CA-G. All trials with this designation indicate that the trial was conducted in California under greenhouse conditions. Weeds in the cotyledonary stage of growth were treated in a precision application chamber designed specifically to test the efficacy of chemical and microbial herbicides. The application chamber utilizes carbon dioxide to pressurize the test material. The test material is delivered to the plants through a standard flat fan spray nozzle (Tee Jet 8002, Spraying Systems Co., Wheaton, Ill.) at a carrier rate of 25 gal/A. After treatment, the plants are placed into a mist chamber for 7 to 14 days. The percentage of plants which are dead or severely damaged (unlikely to survive) is recorded as percent weed control.

Florida: FL-F. The Florida field trial was carried out under permits from the USDA and the State of Florida. The test materials were applied in the morning and the trial was irrigated at dusk. Applications were made with the aid of a field backpack sprayer calibrated to apply 25 gal/A.

Illinois: IL-F. The Illinois field trial was carried out under permits from the USDA and the State of Illinois. The test materials were applied with the aid of a field backpack sprayer calibrated to apply 50 gal/A. Plants were treated in the four leaf stage of growth.

Montreal: ML-C. Weeds in the cotyledon, one, or two leaf stage of development were treated with solutions of test material to run-off. The rate of compounds in the spray solutions was based upon an application volume of 100 gal/A. Inoculated plants were placed into a dew chamber for 18 hr, then removed and placed in a controlled environment chamber. Evaluations were made after 20 to 45 days and the percentage of the total number of plants which were killed was recorded as percent weed control.

Montreal: ML-G. Weeds in the cotyledon, one, or two leaf stage of development were treated with solutions of test material to run-off. The rest of compounds in the spray solutions was based upon an application volume of 100 gal/A. Inoculated plants were placed into a dew chamber for 18 hr, then removed and placed in a controlled environment chamber. Evaluations were made after 20 to 45 days and the percentage of the total number of plants which were killed was recorded as percent weed control.

Montreal: ML-F. Field grown weeds in the cotyledon, one, or two leaf stage of development were treated with the test compounds in situ. Applications were made in a carrier volume of 100 gal/A. The percentage of the total number of plants which were killed was recorded as percent weed control.

Vermont: VT-F. Trials were applied using the same techniques described in the Montreal field trails (ML-F).

The weed abbreviations listed below are those accepted and reported in the Composite List of Weeds, Weed Science (1984) 2:Supp. 2.

ABUTH = *Abutilon theophrasti* Medik.
CASOB = *Cassia obtusifolia* L.
DEDTO = *Desmodium tortuosum* (Sw.) DC.

The abbreviation used for *Colletotrichum coccodes* is:
CC = *Colletotrichum coccodes*.

Following are examples which illustrate procedures, including the best mode, for practicing the invention. These examples should not be construed as limiting. All percentages are by weight and all solvent mixture proportions are by volume unless otherwise noted.

EXAMPLE 1

Basagran in Combination with AC, CC, CT, and FL

Basagran is a herbicide of broadleaf plants. This herbicide is a sodium salt of an organic acid. Basagran produces synergistic activity in controlling velvetleaf when mixed with *C. coccodes*, in spite of the known detrimental effect of this herbicide on growth of *C. coccodes*.

With regard to the tables in this Example and the Examples following, application rates for microbial herbicides as expressed as PPA (propagules per acre)$\times 10^9$. Application rates for chemicals are expressed as pounds of active ingredient per acre.

TABLE 1

| Microbial Herbicide | Weed | Trial Loc-Type | Application Rate Microbial | Application Rate Chemical | Percent Weed Control Microbial | Percent Weed Control Chemical | Percent Weed Control Tank Mix |
|---|---|---|---|---|---|---|---|
| AC | CASOB | CA-G | 0.57 | 0.05 | 0 | 0 | 86 |
| CC | ABUTH | IL-F | 4100.00 | 0.75 | 10 | 13 | 65 |
| CC | ABUTH | ML-C | 4100.00 | 0.30 | 67 | 8 | 92 |
| CC | ABUTH | VT-F | 4100.00 | 0.75 | 7 | 40 | 79 |
| CT | DEDTO | CA-G | 9.30 | 0.30 | 41 | 0 | 71 |
| FL | ABUTH | CA-G | 410.00 | 0.05 | 0 | 38 | 65 |

EXAMPLE 2

Blazer in Combination with AC, CC, CT, and FL

Blazer is another example of a broadleaf chemical herbicide which is a salt of an organic acid. The environmental conditions during a majority of the experiments was limiting and the microbial herbicides demonstrated little or no weed control activity on their respective hosts. The inhibition of AC and CT spore germination and the reduction in growth of CC was much less than observed with the combinations with Basagran.

TABLE 2

| Microbial Herbicide Mix | Weed | Trial Loc-Type | Application Rate Microbial | Application Rate Chemical | Percent Weed Control Microbial | Percent Weed Control Chemical | Percent Weed Control Tank |
|---|---|---|---|---|---|---|---|
| AC | CASOB | CA-G | 0.57 | 0.05 | 0 | 0 | 86 |
| CC | ABUTH | VT-F | 4100.00 | 0.40 | 7 | 43 | 62 |
| CT | DEDTO | CA-G | 9.30 | 0.05 | 0 | 0 | 94 |
| FL | ABUTH | CA-G | 410.00 | 0.05 | 0 | 0 | 20 |

EXAMPLE 3

Classic in Combination with AC, CC, and CT

Classic is a broadleaf herbicide which is an ester. This herbicide is clearly antagonistic to the activity of AC when the mixture is applied to control sicklepod. Classic does not severely inhibit the spore germination of AC, indicating that the antagonistic interaction is possibly affecting the physiology of the interaction between AC and the sicklepod plant. An example might include interference with stomatal opening which would make penetration of AC into the leaf more difficult.

Classic is synergistic in controlling weeds when applied in combination with CC, or CT. Both of these fungi are capable of penetrating the leaf directly (without the need for a wound or open stomates).

TABLE 3

| Microbial Herbicide | Weed | Trial Loc-Type | Application Rate Microbial | Application Rate Chemical | Percent Weed Control Microbial | Percent Weed Control Chemical | Percent Weed Control Tank Mix |
|---|---|---|---|---|---|---|---|
| AC | CASOB | CA-G | 0.29 | 0.02 | 31 | 4 | 21 |
| CC | ABUTH | ML-C | 4100.00 | 0.01 | 0 | 0 | 58 |
| CC | ABUTH | ML-F | 4100.00 | 0.02 | 0 | 8 | 37 |
| CT | DEDTO | FL-F | 31.00 | 0.02 | 0 | 16 | 49 |

*C. coccodes* was further tested in mixture with acifluorfen (BLAZER), bentazon (BASAGRAN), and chlorimuron (CLASSIC). The procedures and results are shown in Example 4.

EXAMPLE 4

*C. coccodes* Plus Acifluorfen, Bentazon, and Chlorimuron

The interactions between *C. coccodes* and chemical herbicides have been conducted in the laboratory, in controlled environment chambers, in mist frames within a greenhouse and in the field. The pathogen is cultured in liquid media for approximately one week after which the fungal spores are separated from the culture media and used as inoculum. The spores are resuspended in water and sprayed with or without added chemical herbicides at various test rates and concentrations.

The fungus *C. coccodes* alone can kill velvetleaf plants when applied at an appropriate concentration and under appropriate environmental conditions. *C. coccodes* can also be tank mixed with chemical herbicides and the control of velvetleaf is usually enhanced. Field trials indicated that tank mix combinations of *C. coccodes* with acifluorfen and bentazon improved velvetleaf control when compared to any product applied alone (Table 4).

In laboratory experiments designed to determine the response of tank mix combinations of chemical herbicides and *C. coccodes*, the new broadleaf soybean herbicide, chlorimuron (DPX-F6025), was synergistic with *C. coccodes* over most of the ranges tested (Tables 5 and 6). Similarly, when bentazon was applied at 5 rates with or without *C. coccodes* at $10^9$ spores/m$^2$ at the 1-2 leaf stage of growth, velvetleaf mortality and biomass reduction were increased significantly when the tank mix of bentazon plus *C. coccodes* was compared to bentazon alone (Tables 7 and 8).

TABLE 4

Velvetleaf control in soybean field trials.

| Treatment | Rate (Spores/m$^2$) (kg/ha) | Fresh wt. (g) | Dry wt. (g) | Mortality (%) |
|---|---|---|---|---|
| Control | — | 1259.4 | 297.2 | 0 |
| C. coccodes | $10^9$ | 880.4 | 189.9 | 7 |
| Acifluorfen | 0.6 | 791.0 | 156.5 | 43 |
| Acifluorfen + C. coccodes | $0.6 + 10^9$ | 449.7 | 96.7 | 62 |
| Bentazon | 1.0 | 496.3 | 112.0 | 40 |
| Bentazon + C. coccodes | $1.0 + 10^9$ | 145.7 | 22.3 | 79 |

[a]Values in the table represent mean percent mortality of 4 replicates of three plants each. Plants were treated at the 1-2 leaf stage, placed in a dew chamber for 18 hours at 24 C, then incubated in a mist frame in the greenhouse which maintained moisture on the leaves for the 12-hour night period.

TABLE 5

*C. coccodes* plus chlorimuron effect on velvetleaf mortality[a]

| Chlorimuron rate (kg a.i./ha) | *Colletotrichum coccodes* rate (spores/m$^2$) | | | | |
|---|---|---|---|---|---|
| | none | $10^6$ | $10^7$ | $10^8$ | $10^9$ |
| | | | % mortality | | |
| none | | | | | |
| 0.0005 | 0 | 0 | 0 | 0 | 0 |
| 0.001 | 0 | 0 | 0 | 0 | 0 |
| 0.005 | 0 | 0 | 0 | 0 | 8 |
| 0.01 | 8 | 8 | 17 | 8 | 92 |

[a]Values in the table represent mean percent mortality of 4 replicates of 3 plants each. Plants were treated at the 1-2 leaf stage, placed in a dew chamber for 18 hours at 24 C, then incubated in a mist frame in the greenhouse which maintained moisture on the leaves for the 12-hour night period.

TABLE 6

*C. coccodes* plus chlorimuron effect on velvetleaf above-ground biomass[a]

| Chlorimuron rate (kg a.i./ha) | *Colletotrichum coccodes* rate (spores/m$^2$) | | | | |
|---|---|---|---|---|---|
| | none | $10^6$ | $10^7$ | $10^8$ | $10^9$ |
| | | | g | | |
| none | 1.12 | 1.36 | 1.21 | 1.14 | 0.82 |
| 0.0005 | 1.06 | 1.26 | .93 | .89 | .73 |
| 0.001 | 1.26 | .90 | 1.11 | 1.08 | .77 |
| 0.005 | .36 | .28 | .73 | .62 | .24 |
| 0.01 | .13 | .31 | .18 | .29 | trace |

[a]Values in the table represent mean above-ground dry weight yield of 4 replicates of 3 plants each. Plants were treated at the 1-2 leaf stage, placed in a dew chamber for 18 hours at 24 C, then incubated in a mist frame in the greenhouse which maintained moisture on the leaves for the 12-hour night period.

TABLE 7

Effect of *C. coccodes* on the level of control of velvetleaf with bentazon[a]

| Bentazon rate (kg a.i./ha) | *Colletotrichum coccodes* rate (spores/m$^2$) | |
|---|---|---|
| | none | $10^9$ |
| | % mortality | |
| none | 0 | 67 |
| 0.1 | 8 | 75 |
| 0.25 | 8 | 92 |
| 0.5 | 83 | 100 |
| 1.0 | 92 | 100 |

[a]Values in the table represent mean percent mortality of 4 replicates of 3 plants each. Plants were treated at the 1-2 leaf stage, placed in a dew chamber for 18 hours at 24 C, then incubated in a mist frame in the greenhouse which maintained moisture on the leaves for the 12-hour night period.

TABLE 8

Effect of *C. coccodes* on the efficacy of bentazon to velvetleaf biomass[a]

| Bentazon rate (kg a.i./ha) | Colletotrichum coccodes rate (spores/m$^2$) | |
|---|---|---|
| | none | 10$^9$ |
| | g | |
| none | 0.58 | 0.13 |
| 0.1 | 0.26 | 0.19 |
| 0.25 | 0.32 | 0.04 |
| 0.5 | 0.05 | 0 |
| 1.0 | trace | 0 |

[a]Values in the table represent mean above-ground dry weight of 4 replicates of 3 plants each. Plants were treated at the 1-2 leaf stage, placed in a dew chamber for 18 hours at 24 C, then incubated in a mist frame in the greenhouse which maintained moisture on the leaves for the 12-hour night period.

*C. coccodes* was tested further with the chemical herbicides dicamba, AC 263,499, DPX M6316, 2,4-D, atrazine, fomesafen, and triasulfuron. The procedure and results are shown in Example 5.

EXAMPLE 5

*C. coccodes* Plus Dicamba, AC 263,499, DPX M6316, 2,4-D, Atrazine, Fomesafen, and Triasulfuron Germinated velvetleaf seeds (48 hr on moist filter paper at 5 C., then 24 hr at 30 C.) were sown 4 per pot in 10 cm plastic pots in potting medium (ProMix BX, Premier Brands, Inc.) and grown in growth chambers (24/18 C. day/night temperature, 14-hour photoperiod, 250 uEm$^{-2}$sec$^{-1}$). Plants were thinned to a final density of 3 per pot and were at the 2 to 4 leaf (14 to 21 days post planting) stage when experimental treatments were applied.

*C. coccodes* was grown in liquid culture in modified Richard's V-8 medium for 7 days and spores were harvested by pouring the culture through 4 layers of cheesecloth, centrifuging the spore suspension (7000 rpm for 10 min) and resuspending the spores in distilled water. Inoculum density was determined with the use of a hemocytometer.

*C. coccodes* and herbicides were applied to plants using a spray camber with a full cone nozzle (TG 0.7) 200 kPa air pressure, speed of 0.85 kph and a spray volume of 500 L of water/ha.

Immediately following inoculation with *C. coccodes*, pots were placed in a dew chamber for 18 hr (24 C. air temperature). Pots were then placed in the greenhouse in a mist frame which maintained moisture on the leaves for a 12-hour period each night. There were 4 pots (12 plants) per treatment. Plants were rated for mortality and harvested 3 to 4 weeks after treatment. Mortality data were recorded as percentages for each of the 4 pots. Biomass of above-ground living tissue was determined by cutting the live plants at the cotyledonary node, drying in paper bags for 7 days at 60 C., and weighing. Biomass data were recorded as total yield for each of the 4 pots. All experiments were repeated twice.

The results of the three experiments for each of the herbicide/*C. coccodes* combinations are presented as means for control (no treatment), *C. coccodes* at 10$^9$ conidia/m$^2$, herbicide (at rate specified in Tables) and *C. coccodes*+the herbicide combination.

TABLE 9

Synergistic interaction between *C. coccodes* and dicamba for velvetleaf control.

| | Mortality (%) | Biomass (g) |
|---|---|---|
| Control | 0 | 2.18 |
| CC (10$^9$ spores/m$^2$) | 0 | 1.50 |
| Dicamba (.32 kg/ha) | 53 | 0.16 |
| CC (10$^9$ spores/m$^2$) + dicamba (.32 kg/ha) | 86 | 0.01 |

TABLE 10

Synergistic interaction between *C. coccodes* and AC 263,499 for velvetleaf control.

| | Mortality (%) | Biomass (g) |
|---|---|---|
| Control | 0 | 1.26 |
| CC (10$^9$ spores/m$^2$) | 0 | 0.54 |
| AC 263,499 (100 g/ha) | 24.7 | 0.09 |
| CC (10$^9$ spores/m$^2$) + AC 263,499 (100 g/ha) | 64 | 0.04 |

TABLE 11

Synergistic interaction between *C. coccodes* and DPX M6316 for velvetleaf control.

| | Mortality (%) | Biomass (g) |
|---|---|---|
| Control | 0 | 2.97 |
| CC (10$^9$ spores/m$^2$) | 2.7 | 1.67 |
| DPX M6316 (12 g/ha) | 5.3 | 0.30 |
| CC (10$^9$ spores/m$^2$) + DPX M6316 (12 g/ha) | 36.3 | 0.12 |

TABLE 12

Synergistic interaction between *C. coccodes* and 2,4-D for velvetleaf control.

| | Mortality (%) | Biomass (g) |
|---|---|---|
| Control | 0 | 1.58 |
| CC (10$^9$ spores/m$^2$) | 0 | 1.23 |
| 2,4-D (400 g/ha) | 24.6 | 0.44 |
| CC (10$^9$ spores/m$^2$) + 2,4-D (400 g/ha) | 36.0 | 0.17 |

TABLE 13

Synergistic interaction between *C. coccodes* and atrazine for velvetleaf control.

| | Mortality (%) | Biomass (g) |
|---|---|---|
| Control | 0 | 1.84 |
| CC (10$^9$ spores/m$^2$) | 0 | 1.23 |
| Atrazine (400 g/ha) | 5.7 | 0.30 |
| CC (10$^9$ spores/m$^2$) + atrazine (400 g/ha) | 14.0 | 0.29 |

TABLE 14

Synergistic interaction between *C. coccodes* and fomesafen for velvetleaf control.

| | Mortality (%) | Biomass (g) |
|---|---|---|
| Control | 0 | 2.73 |
| CC (10$^9$ spores/m$^2$) | 0 | 2.65 |
| Fomesafen (0.20 kg/ha) | 47 | 0.48 |
| CC (10$^9$ spores/m$^2$) + fomesafen (0.20 kg/ha) | 61 | 0.37 |

TABLE 15

Synergistic interaction between *C. coccodes* and triasulfuron for velvetleaf control.

| | Mortality (%) | Biomass (g) |
|---|---|---|
| Control | 0 | 2.70 |
| CC ($10^9$ spores/$m^2$) | 0 | 2.62 |
| Triasulfuron (0.008 kg/ha) | 54.5 | 0.31 |
| CC ($10^9$ spores/$m^2$) + triasulfuron (0.008 kg/ha) | 88 | 0.06 |

Synergistic results with mixtures of *C. coccodes* and 2,4-DB, lactofen, and glyphosate, tested under the conditions given above, are presently being compiled.

We claim:

1. A composition of matter for controlling velvetleaf comprising a synergistic mixture of a chemical herbicide selected from the group consisting of bentazon sodium salt, acifluorfen sodium salt, 2,4-D, DPX-F6025, dicamba, AC 263.499, DPX M6316, atrazine, fomesafen, triasulfuron, 2,4-DB, lactofen, and glyphosate, and the velvetleaf isolate of *Colletotrichum coccodes*.

2. The composition, according to claim 1, wherein said chemical herbicide is DPX-F6025.

3. A process for controlling velvetleaf comprising applying an herbicidally effective amount of a synergistic herbicidal composition of (1) a chemical herbicide selected from the group consisting of bentazon sodium salt, acifluorfen sodium salt, 2,4-D, DPX-F6025, dicamba, AC 263.499, DPX M6316, atrazine, fomesafen, triasulfuron, 2,4-DB, lactofen, and glyphosate, and (2) the velvetleaf isolate of *Collectotrichum coccodes* to said velvetleaf or unto the situs of the velvetleaf.

4. The process, according to claim 3, wherein the chemical herbicide is DPX-F6025.

* * * * *